United States Patent [19]

Stahl

[11] Patent Number: 5,544,754

[45] Date of Patent: Aug. 13, 1996

[54] DENTAL APPLIANCE

[76] Inventor: Kevin J. Stahl, 311 Fulton Ave., Rochester, Ind. 46975

[21] Appl. No.: 283,826

[22] Filed: Aug. 1, 1994

[51] Int. Cl.[6] ............................ A61C 15/00; B65D 69/00
[52] U.S. Cl. ........................ 206/581; 132/323; 132/324; 206/277
[58] Field of Search ........................ 206/581, 277; 222/93, 106, 192; 132/308, 309, 310, 311, 324, 325, 323

[56] References Cited

U.S. PATENT DOCUMENTS

| 301,055 | 6/1884 | Greene | 132/309 X |
|---|---|---|---|
| 1,454,429 | 5/1923 | Dresser | 132/325 X |
| 2,601,244 | 6/1952 | Boulicault | 132/309 |
| 3,782,397 | 1/1974 | McCord | 132/311 X |
| 4,428,389 | 1/1984 | Sanchez Cordero | 132/325 |
| 4,598,839 | 7/1986 | Dombroski et al. | 222/106 |
| 4,705,194 | 11/1987 | Judge | 222/93 |
| 4,827,951 | 5/1989 | Grossmark | 132/324 X |
| 5,176,157 | 1/1993 | Mazza | 132/325 X |
| 5,348,028 | 9/1994 | Gustavel | 132/308 X |

*Primary Examiner*—Paul T. Sewell
*Assistant Examiner*—Tara Laster
*Attorney, Agent, or Firm*—Lundy and Associates

[57] ABSTRACT

In the broader aspects of the invention, there is provided an improved dental appliance comprising a dentifrice package with an applicator at one package end and a hollow base at the other package end. A supply of dentifrice is positioned in the package. A supply of dental floss is positioned within the hollow base and threaded through an exit opening in the base.

10 Claims, 1 Drawing Sheet

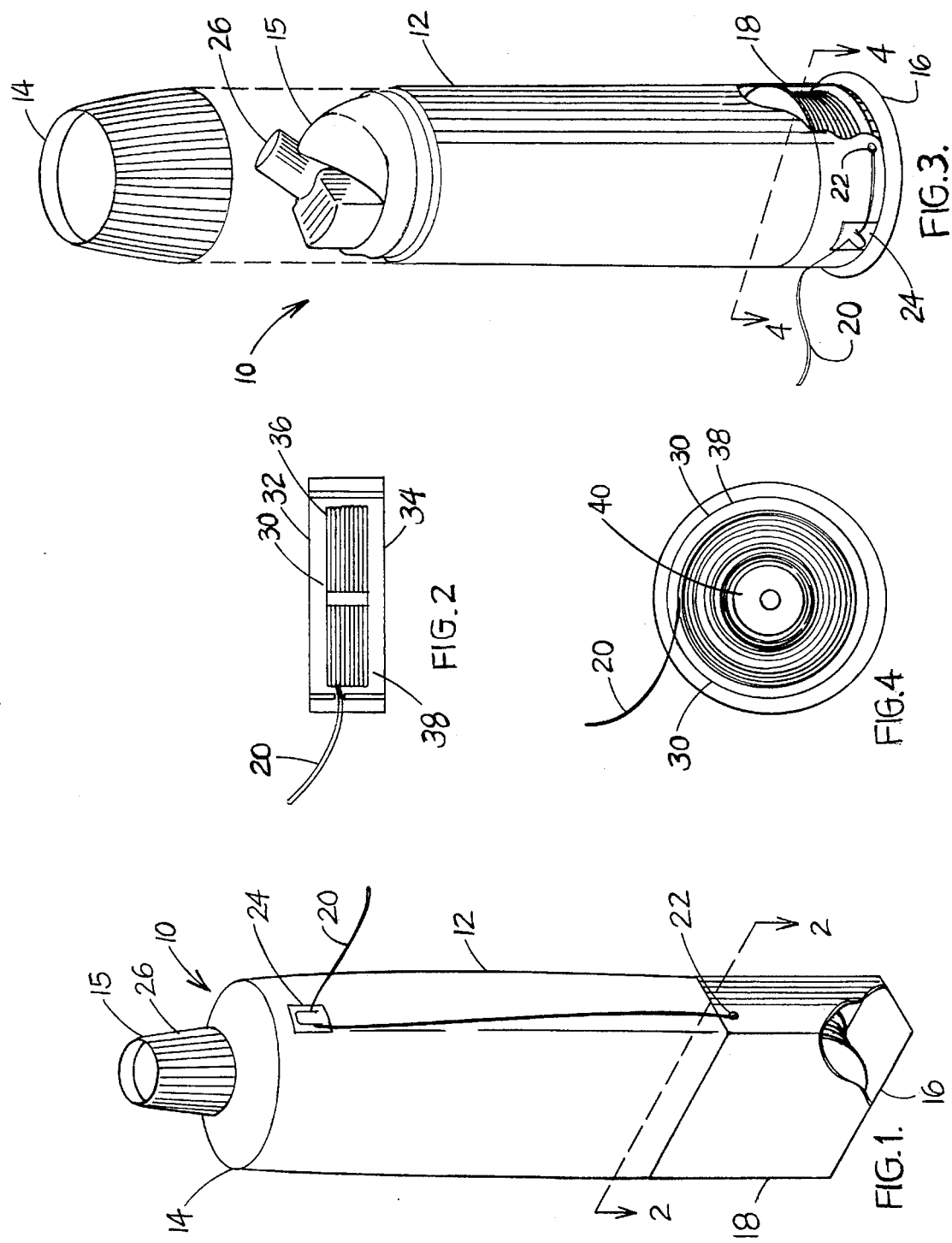

DENTAL APPLIANCE

BACKGROUND OF THE INVENTION

The present invention relates to a new and improved dental appliance, and more particularly to a dental appliance from which both dentifrice and dental floss may be dispensed and utilized to clean teeth.

Dentists have long been recommending to their patients routine brushing and flossing of teeth to maintain the teeth clean and the gums healthy. Heretofore, dentifrice and dental floss have been sold in separate packages. In general, the dentists have promoted flossing and tooth brushing as separate care options. Brushing after every meal has been recommended for decades. Flossing daily has been recommended for decades. However, combining flossing and brushing has not been promoted together, nor has there been an appliance which would facilitate or make convenient the use of both at the same time.

Packaging for both dentifrice and dental floss has changed over the years. No package has been preferred by all.

It is therefore highly desirable to provide an improved package for dentifrice and dental floss.

It is also highly desirable to provide an improved dental appliance which promotes the use of brushing teeth with a dentifrice and using floss between the teeth as routine dental care after each meal.

It is also highly desirable to provide an improved dental appliance which fosters the efficient use of both dentifrice and dental floss.

It is also highly desirable to provide an improved package for dentifrice and dental floss which is inexpensive to manufacture and convenient to use.

It is finally highly desirable to provide an improved dental appliance having all of the above features.

SUMMARY OF THE INVENTION

It is therefore an of object of the invention to provide an improved package for dentifrice and dental floss.

It is also an object of the invention to provide an improved dental appliance which promotes the use of brushing teeth with a dentifrice and using floss between the teeth as routine dental care after each meal.

It is also an object of the invention to provide an improved dental appliance which fosters the efficient use of both dentifrice and dental floss.

It is also an object of the invention to provide an improved package for dentifrice and dental floss which is inexpensive to manufacture and convenient to use.

It is finally an object of the invention to provide an improved dental appliance having all of the above features.

In the broader aspects of the invention, there is provided an improved dental appliance comprising a dentifrice package with an applicator at one package end and a hollow base at the other package end. A supply of dentifrice is positioned in the package. A supply of dental floss is positioned within the hollow base and threaded through an exit opening in the base.

BRIEF DESCRIPTION OF THE INVENTION

The above-mentioned and other features and objects of the invention and the manner of attaining them will become more apparent and the invention itself will be better understood by reference to the following description of an embodiment of the invention taken in conjunction with the accompanying drawings wherein:

FIG. 1 is a perspective view of the improved dental appliance of the invention including a squeeze tube dispenser of dentifrice.

FIG. 2 is a cross-sectional view of the improved dental appliance of the invention taken essentially along the section line 2—2 of FIG. 1.

FIG. 3 is a perspective view of the improved dental appliance of the invention including a pump dentifrice dispenser.

FIG. 4 is a cross-sectional view of the improved dental appliance of FIG. 3 taken essentially along section lines 4—4.

DESCRIPTION OF A SPECIFIC EMBODIMENT

The improved dental appliance 10 of the invention comprises an elongated dentifrice package 12 having opposite ends 14, 16 and a longitudinal axis 17. Dentifrice 13 is placed in the package 12. Adjacent end 14 is a dentifrice dispenser 15. Adjacent end 16 is a hollow base 18 in which is positioned a supply of dental floss 20. Appliance 10 has an exit opening 22 adjacent end 16 through which the floss 20 is threaded. Secured to the exterior of package 12 is a dental floss cutter 24 spaced from the exit opening 22.

In the specific embodiments illustrated in FIG. 1, the dentifrice package 12 is a squeeze tube in which dentifrice is packaged and dispensed through a tubular screw cap opening 26. At end 16, there is provided a base 18 in the form of a relatively thin square box in which a spool 30, having dental floss 20 wound thereon, is positioned. Box 18, in the embodiment illustrated, has sides of approximately the same length as the transverse dimension of squeeze tube package 12. Package 12 has an exit opening 22 in the box adjacent end 16 through which floss is dispensed as spool 30 rotates. The axis 28 about which the spool 30 rotates is generally perpendicular to the axis of package 12. Base 18 is relatively rigid and can be utilized to fold the squeeze tube 12 as it is being dispensed in a conventional fashion to efficiently empty the package 12. A dental floss cutter 24 is positioned adjacent end 14 such that when floss is stretched from base 18 to cutter 24 once, or multiple times, an efficient length of floss is dispensed.

FIGS. 3 and 4 disclose the improved appliance 10 of the invention having a pump dispenser 15 for dentifrice at end 14 and a hollow base 18 at end 16. Within the hollow base 18 is positioned a spool 30 around which dental floss 20 is wound. Dental floss 20 is trained through and dispensed from exit opening 22. The axis 28 about which the spool 30 rotates is generally coaxial with the longitudinal axis of package 12. Exit opening 22 is adjacent end 16. A floss cutter 24 is positioned on the exterior surface of the package 12 adjacent end 16. The package 12 is cylindrical in shape having a diameter of a sufficient size such that when the dental floss 20 is pulled from spool 30 through the opening 22 and wound around the package 12 once or multiple times and cut, an efficient length of dental floss 20 is dispensed. In a specific embodiment, package 12 has a diameter equal to from about 0.5 to 0.75 of the minimum usable length of floss, such that floss dispensed from package 12 may be wound about the package 12 one and one-half rotations and cut by the floss cutter to dispense an efficient length of usable floss.

In both of the appliances 10 disclosed, the base 18 includes a surface 32 and a surface 34. Within the base 18 is a spool 30 having a barrel 40 and opposite flanges, 36, 38, one of which is adjacent surface 32 and the other of which is adjacent surface 34. Spool 30 is contained with base 18 loosely such that spool 30 may rotate within the confines of base 18. In both of the dental appliances disclosed, the friction between flanges 36, 38 and surfaces 32, 34 provides tension on the floss being dispensed such that spool 30 never over rotates to entangle the floss within base 18. In a specific embodiment, said spool comprises the plunger of the pump of the pump dispenser 15.

In operation, the improved dental appliance 10 of the invention may be used to dispense both dentifrice and dental floss as desired. To dispense the dentifrice of the embodiment illustrated in FIGS. 1 and 2, the tube is squeezed as is conventional. Base 18 is rigid and may be folded against the tube and the tube folded around the base 18 with the tube squeezed between the base 18 and a solid surface, such as a countertop, to dispense all of the dentifrice from the package 12 through the tubular cap opening 26. Dental floss 20 may be dispensed from end 16 of the package shown in FIGS. 1 and 2 through the exit opening 22. Dental floss 20 may be dispensed through exit opening 22 and extended lengthwise of the tube, one or multiple times, to the dental floss cutter 24 by which floss 20 is cut, thus dispensing an efficient length of floss 20 for use. Dentifrice can be dispensed from the package 12 of the embodiment shown in FIGS. 3 and 4 by pumping the pump 15 as is conventional. All of the dentifrice can be dispensed from the package 12 in this manner. Dental floss 20 may be dispensed from the base 18 through exit opening 22 and extended around the package 12 one or multiple times, and cut by floss cutter 24 to dispense efficient lengths of floss 20 for use. The improved dental appliance of the invention provides an improved package for both dentifrice and dental floss. The package promotes the use of brushing and flossing together as routine dental care after each meal. The package fosters efficient use of both dentifrice and dental floss and is relatively inexpensive to manufacture and convenient to use. While a specific embodiment of the invention has been shown and described herein for purposes of illustration, the protection afforded by any patent which may issue upon this application is not strictly limited to the disclosed embodiment; but rather extends to all structures and arrangements which fall fairly within the scope of the claims which are appended hereto:

What is claimed is:

1. A dental appliance comprising an elongated dentifrice package, said package having opposite ends and a longitudinal axis, a dentifrice dispenser at one of said package ends, said dispenser and package being a squeeze tube, a hollow base being secured to said package at the other of said package ends, a winding of dental floss positioned within said base, an exit opening adjacent said other of said package ends through which said floss is threaded, and a floss cutter on said package spaced from said exit opening, whereby floss may be dispensed from said package and measured against said package between said exit opening and said cutter to dispense floss and said package may be wound about said base and squeezed against said base to empty said package of dentifrice.

2. The dental appliance of claim 1 wherein said dental floss is wound about a spool.

3. The dental appliance of claim 2 wherein said package is tubular, whereby said floss dispensed from said package may be wound about said package multiple times and cut by said floss cutter to dispense floss.

4. The dental appliance of claim 2 wherein said spool has a barrel and two flanges secured to the opposite ends of the barrel, said barrel spaces apart said flanges and provides a space therebetween in which floss may be wound, said spool being positioned in said hollow base, said hollow base having spaced apart surfaces, one of said flanges being adjacent to one of said spaced surfaces, the other of said flanges being adjacent to another of said spaced surfaces, said spool being loosely positioned within said base between said spaced surfaces, said surfaces guiding the rotation of said spool relative to said base as said floss is unwound from said spool through said exit opening.

5. The dental appliance of claim 4 wherein said spool generally rotates about an axis generally perpendicular of said axis of said package.

6. The dental appliance of claim 7 wherein said spool rotates about said axis.

7. A dental appliance comprising an elongated dentifrice package, said dentifrice package being a pump with a plunger, said package having a floss cutter thereon, said package having opposite ends and a longitudinal axis, a dentifrice dispenser at one of said package ends, a hollow base being at the other of said package ends, a winding of dental floss positioned within said base, said dental floss being wound about a spool, said spool comprises said plunger of said pump, an exit opening adjacent said other of said package ends through which said floss is threaded, and a floss cutter on said package spaced from said exit opening, whereby floss may be dispensed from said package and measured against said package between said exit opening and said cutter to dispense lengths of floss.

8. The dental appliance of claim 7 wherein said package is tubular whereby said floss dispensed from said package may be wound about said package multiple times and cut by said floss cutter to dispense floss.

9. The dental appliance of claim 7 wherein said package is tubular, whereby said floss dispensed from said package may be wound about said package multiple times and cut by said floss cutter to dispense floss, said dental floss being wound about a spool, said spool has a barrel and two flanges secured to the opposite ends of the barrel, said barrel spaces apart said flanges and provides a space therebetween in which floss may be wound, said spool being positioned in said hollow base, said hollow base having spaced surfaces, one of said flanges being adjacent to one of said spaced surfaces, the other of said flanges being adjacent to another of said spaced surfaces, said spool being loosely positioned within said base, said surfaces guiding the rotation of said spool relative to said base as said floss is unwound from said spool through said exit opening.

10. A dental appliance comprising an elongate dentifrice package, said package having opposite ends and a longitudinal axis, a dentifrice dispenser at one of said package ends, said dentifrice dispenser being a pump with a plunger, said package has a floss cutter thereon, a hollow base being at the other of said package ends, a winding of dental floss positioned within said base; said dental floss being wound about a spool, said spool generally rotates about said axis, an exit opening adjacent said other of said package ends through which said floss is threaded, said floss cutter being spaced from said exit opening, said package being tubular and has a diameter whereby floss dispensed from said package may be wound about said package and measured between said exit opening and said cutter to dispense lengths of floss, said spool comprises said plunger of said pump.

* * * * *